(12) United States Patent
Rafter et al.

(10) Patent No.: US 6,730,036 B2
(45) Date of Patent: May 4, 2004

(54) ULTRASONIC IMAGING TO DETECT CORONARY ARTERY STENOSIS AT REST

(75) Inventors: Patrick G. Rafter, Windnam, NH (US); Jerome F. Witt, Andover, MA (US); Sanjiv Kaul, Charlottesville, VA (US); Kevin Wei, Charlotesville, VA (US); George A. Brock-Fisher, Andover, MA (US)

(73) Assignees: Koninklijke Philips Electronics, N.V., Eindhoven (NL); University of Virginia, Charlottsville, VA (US)

(*) Notice: Subject to any disclaimer, the term of this patent is extended or adjusted under 35 U.S.C. 154(b) by 0 days.

(21) Appl. No.: 10/086,027

(22) Filed: Feb. 28, 2002

(65) Prior Publication Data

US 2003/0163048 A1 Aug. 28, 2003

(51) Int. Cl.[7] ................................. A61B 8/14
(52) U.S. Cl. .................................... 600/458
(58) Field of Search ............... 600/407–471; 73/625, 626; 367/7, 11, 130, 138; 128/916; 424/9.351, 9.35, 9.51, 9.52, 617, 9.34

(56) References Cited

U.S. PATENT DOCUMENTS 5,833,613 A * 11/1998 Averkiou et al. ........... 600/440
5,944,666 A * 8/1999 Hossack et al. ............ 600/458
6,315,729 B1 * 11/2001 Averkiou et al. ........... 600/458
6,315,730 B1 * 11/2001 Hoff et al. .................. 600/458

FOREIGN PATENT DOCUMENTS

EP        0770352 A1    5/1997

\* cited by examiner

Primary Examiner—Ali M. Imam
(74) Attorney, Agent, or Firm—John Vodopia

(57) ABSTRACT

Ultrasonic imaging to receive a signal from contrast agent microbubbles in arterioles of a myocardium, without being masked by a signal from microbubbles in capillaries of the myocardium. For example, high power ultrasonic energy is emitted to destroy microbubbles in the arterioles and capillaries. A time delay passes from the destruction. The time delay is sufficiently long to allow the arterioles to refill with microbubbles and sufficiently short so that the capillaries do not completely refill with microbubbles. Ultrasonic imaging is then performed to receive a signal between harmonics from the microbubbles refilled in the arterioles. Various other destructive and non-destructive imaging techniques are disclosed.

32 Claims, 7 Drawing Sheets

ULTRASONIC IMAGING TO DETECT CORONARY ARTERY STENOSIS AT REST

BACKGROUND OF THE INVENTION

1. Field of the Invention

The present invention relates to ultrasonic imaging and, more particularly, to the use of ultrasonic imaging to detect coronary artery stenosis while a patient is at rest.

2. Description of the Related Art

Ultrasonic imaging systems are widely used to produce an image of inside a person's body.

FIG. 1 is a diagram illustrating the general concept of an ultrasonic imaging system. Referring now to FIG. 1, an ultrasonic imaging system 18 typically includes electronics 20 and a transducer 22. Electronics 20 produces control signals for transducer 22. In accordance with the control signals, transducer 22 transmits ultrasonic energy 24 into tissue 26, such as that, for example, in a human body. Ultrasonic energy 24 causes tissue 26 to generate a signal 28 which is received by transducer 22. Electronics 20 then forms an image in accordance with the received signal 28.

Various techniques for ultrasonic imaging include the use of contrast agent microbubbles. Contrast agents microbubbles dramatically enhance backscatter of blood. Their non-linear behavior has allowed manufacturers of ultrasonic imaging systems to develop techniques that image these microbubbles selectively by virtually eliminating tissue signals.

Techniques currently available to image contrast agents microbubbles include real-time techniques (i.e., non-destructive) such as Power Modulation and Pulse Inversion. There are also triggered techniques available (i.e., harmonic imaging, harmonic power Doppler, ultraharmonics) which rely on microbubble destruction.

It is currently not possible for an ultrasonic imaging system to detect a coronary artery stenosis of less than 90% (i.e., 90% or more of the coronary artery is blocked) in a patient at rest. This is due to an autoregulation process that occurs in microcirculation, which allows the body to compensate for a pressure drop across a stenosis by vasodilating arterioles downstream of the stenosis. This compensatory mechanism maintains perfusion pressure and blood flow through the capillaries. As long as blood flow is maintained the heart will function properly and a resting study will not show a wall motion abnormality.

Moreover, with a stenosis of less than 90%, contrast agent microbubbles will not identify a perfusion abnormality, because most of the blood volume (approximately 90%) in a myocardium resides in capillaries and the capillary blood volume does not change with the stenosis. The signals from microbubbles in the capillaries "drown out" the signals from arterioles in an ultrasonic image. Therefore, conventional ultrasonic imaging systems are not effective in detecting a stenosis less than 90% while a patient is at rest.

To detect a stenosis, currently a patient must undergo a stress exam to create a reduction of blood volume within the capillaries (relative to healthy regions). This exam often requires that a patient run on a treadmill or ride a bike, or can require some form of pharmacological stress such a Dobutamine or Dipyridamole, or pacing of the heart. These exams are time consuming, expensive and very difficult on the patient.

It would be very beneficial for ultrasonic imaging systems to detect stenosis of less than 90% without performing such a stress exam.

Work done by Wei et al. on open-chest dogs using harmonic imaging with a high acoustic power and high doses of contrast agent has shown that it is possible to image arterioles with a patient at rest by destroying the microbubbles and relying on the quick refill times of the arterioles. This is due to the fact that the velocity in a capillary is about 1 mm/sec and in an arteriole it is about 50 mm/sec. However, this technique suffers from a poor signal-to noise ratio because of the large tissue signal masking the arteriole signal. Therefore, very large doses of contrast agent were used and the image suffered from attenuation allowing visualization only in the near-field.

SUMMARY OF THE INVENTION

Accordingly, the present invention provides an apparatus and method including (a) destroying contrast agent microbubbles in arterioles and capillaries of a myocardium; and (b) at a time delay from the destruction of the microbubbles which is sufficiently long to cause the arterioles to refill with microbubbles and sufficiently short so that the capillaries do not completely refill with microbubbles, performing ultrasonic imaging to receive an ultrasonic signal between adjacent harmonics, or less than a first harmonic, from microbubbles refilled in the arterioles.

The present invention also provides an apparatus and method including (a) destroying contrast agent microbubbles in arterioles and capillaries of a myocardium; and (b) at a time delay from the destruction of the microbubbles which is sufficiently long to cause the arterioles to refill with microbubbles and sufficiently short so that the capillaries do not completely refill with microbubbles, performing ultrasonic imaging by (i) emitting ultrasonic energy at a fundamental frequency in the myocardium, (ii) receiving a response in the myocardium generated in response to the emitted ultrasonic energy, and (iii) filtering the received response with a filter having a passband between adjacent harmonics of the fundamental frequency and which substantially filters out energy at the adjacent harmonics, or less than a first harmonic and which substantially filters out energy at the first harmonic, to thereby receive a signal from microbubbles refilled in the arterioles.

Moreover, the present invention provides an apparatus and method including (a) destroying contrast agent microbubbles in arterioles and capillaries of a myocardium; and (b) at a time delay from the destruction of the microbubbles which is sufficiently long to cause the arterioles to refill with microbubbles and sufficiently short so that the capillaries do not completely refill with microbubbles, performing ultrasonic imaging using a power Doppler mode to receive a signal from microbubbles refilled in the arterioles.

In addition, the present invention provides an apparatus and method including (a) performing ultrasonic imaging using a non-destructive imaging mode to receive an ultrasonic response which includes a signal from contrast agent microbubbles and a linear tissue signal, the non-destructive imaging mode removing the linear tissue signal from the ultrasonic response, to thereby receive the signal from the microbubbles.

Further, the present invention provides an apparatus and method including (a) transmitting ultrasonic energy into a myocardium at an intensity causing contrast agent microbubbles in arterioles and capillaries of the myocardium to be destroyed; and (b) at a time delay from the destruction of the microbubbles which is sufficiently long to cause the arterioles to refill with microbubbles and sufficiently short so that the capillaries do not completely refill with microbubbles, performing ultrasonic imaging at an intensity lower than said intensity of said transmitted ultrasonic energy.

Advantages of the invention will be set forth in part in the description which follows, and, in part, will be obvious from the description, or may be learned by practice of the invention.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
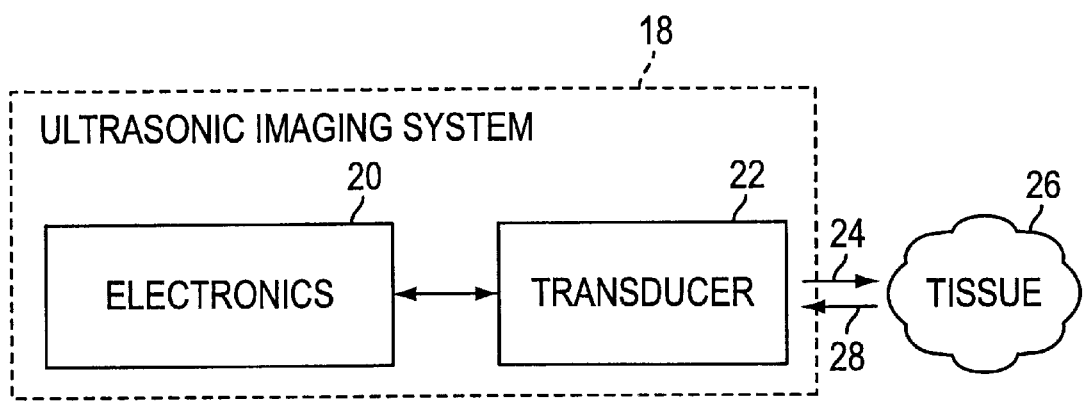
FIG. 1 (prior art) is a diagram illustrating the general concept of an ultrasonic imaging system.

Reference will now be made in detail to the present preferred embodiments of the present invention, examples of which are illustrated in the accompanying drawings, wherein like reference numerals refer to like elements throughout.

Figure 2:
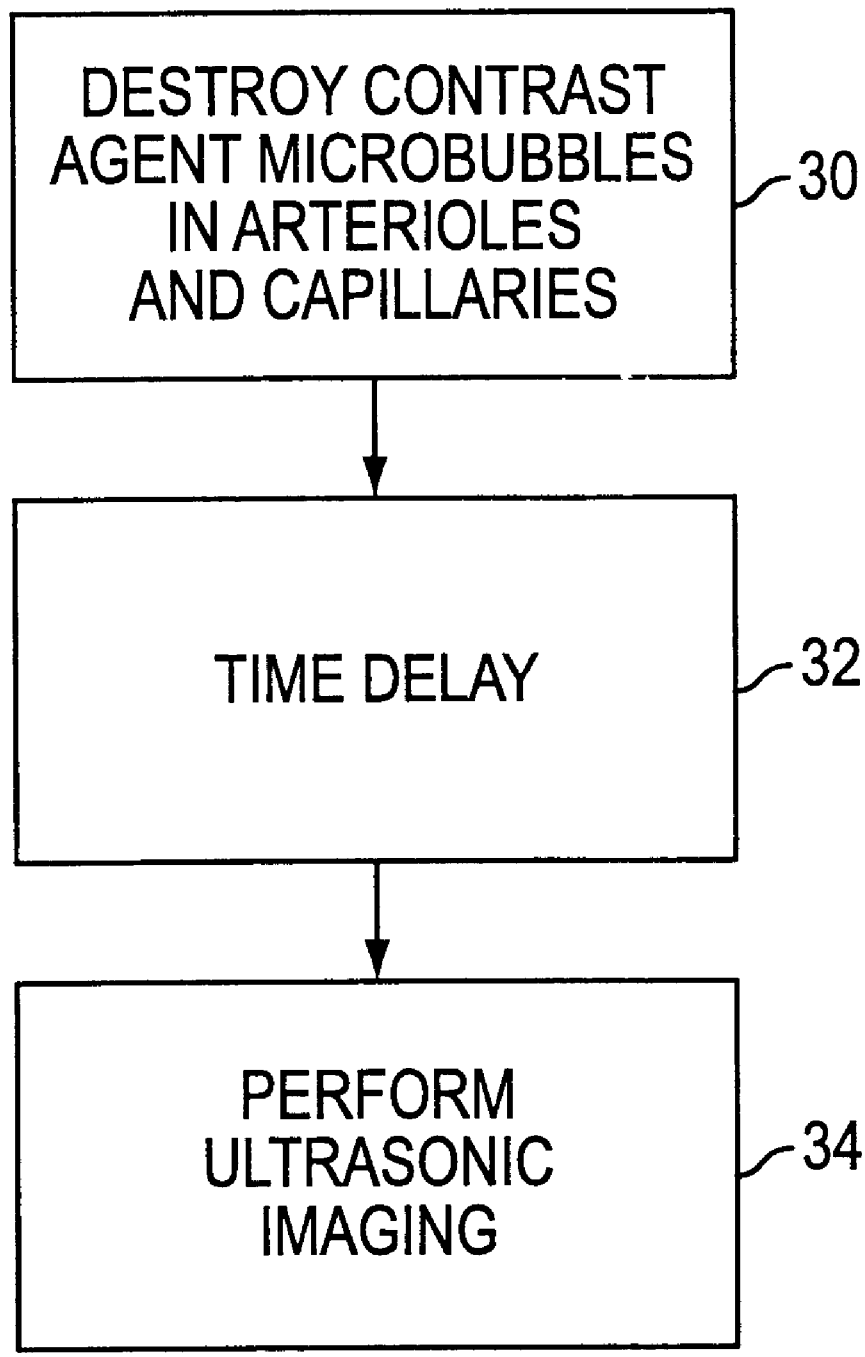
FIG. 2 is a diagram illustrating a destructive imaging process, according to an embodiment of the present invention.

FIG. 2 is a diagram illustrating a destructive imaging process, according to an embodiment of the present invention. Referring now to FIG. 2, in operation 30, contrast agent microbubbles in arterioles and capillaries of a myocardium are destroyed. Such destruction of microbubbles is achieved, for example, by emitting ultrasonic energy into the myocardium at an intensity causing the microbubbles to be destroyed. An appropriate power of the emitted ultrasonic energy sufficient to destroy microbubbles would be easily determinable by a person of skill in the art. Generally, for destructive imaging, the power of the emitted ultrasonic energy should be as high as possible to destroy microbubbles, but within acceptable governmental regulations. Generally, to ensure appropriate microbubble destruction, the mechanical index (MI) should be greater than or equal to 0.5. In a typical, practical application, MI might be greater than or equal to 1.6.

From operation 30, the process moves to operation 32, where a time delay passes from the destruction of the microbubbles. The time delay is sufficiently long to cause the arterioles to refill with microbubbles and sufficiently short so that the capillaries do not completely refill with microbubbles. To achieve the required effect, the time delay might be, for example, greater than 20 ms but less than 4 s. However, the present invention is not limited to the time delay being in this specific range.

From operation 32, the process moves to operation 34, where, at the end of the time delay, ultrasonic imaging is performed to receive a signal from microbubbles refilled in the arterioles. Since the time delay in operation 32 was sufficiently short so that the capillaries do not completely refill with microbubbles, the present invention allows a signal from microbubbles refilled in the arterioles to be received without being masked by a signal from microbubbles in the capillaries. Thus, the present invention takes advantage of the difference in refill times of the arterioles and the capillaries.

The exact length of the time delay in operation 32 can be set in accordance with system design parameters. For example, the time delay may be sufficiently long to allow a partial refilling of microbubbles in the capillaries, but sufficiently short so that the capillaries are not completely refilled. Generally, the time delay should be set so that a signal from microbubbles refilled in the arterioles is not masked by a signal from microbubbles refilled in the capillaries. As indicated above, such a time delay might be, for example, greater than 20 ms but less than 4 s. An appropriate time delay could be determined by a person of skill in the art, based on system design parameters and processing capabilities.

As will be discussed in more detail below, in operation 34, imaging frames can be fired synchronous with an electrocardiogram (ECG). An ECG is derived via a patient connection and ECG monitoring device The ECG monitoring device provides an ECG signal to the ultrasonic imaging system so that the operation of the ultrasonic imaging system can be synchronized to the patient heart cycle. Moreover, as discussed in more detail below, in operation 34, ultrasonic imaging can be performed using a multiple-pulse technique using wall filtering to remove stationary or slow moving signals.

Figure 3:
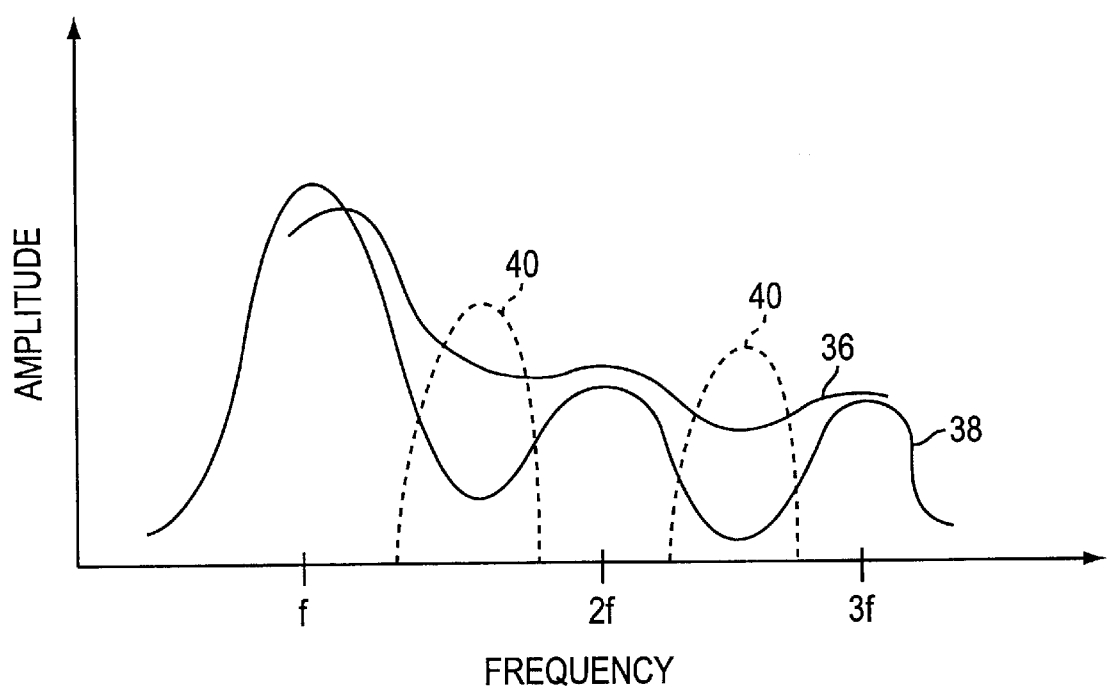
FIG. 3 is a graph illustrating an ultrasonic response in a myocardium generated in response to ultrasonic energy emitted into the myocardium, according to an embodiment of the present invention.

FIG. 3 is a graph illustrating an ultrasonic response in a myocardium generated in response to ultrasonic energy emitted into the myocardium, according to an embodiment of the present invention. Referring now to FIG. 3, the ultrasonic response includes a signal 36 from contrast agent microbubbles and a tissue signal 38. As can be seen from FIG. 3, the amplitude of signal 36 is close to the amplitude of tissue signal 38 at the first harmonic (which is also the fundamental frequency) f and at harmonics $2f$, $3f$ of the fundamental frequency. As a result, it is difficult to distinguish signal 36 from tissue signal 38 at the harmonics f, $2f$ and $3f$.

However, according to an embodiment of the present invention, it is much easier to distinguish signal 36 from tissue signal 38 away from the harmonics. For example, an RF filter 40 can be used to filter out energy around the harmonics. As an example, as shown in FIG. 3, RF filter 40 could be positioned between the first harmonic f and the harmonic $2f$, or between harmonics $2f$ and $3f$. Moreover, in some embodiments, RF filter 40 might be positioned at a frequency less than the first harmonic f. The present invention is not limited to an RF filter being between the specific harmonics discussed herein, or at less then the first harmonic f. It should be understood that many harmonics might be produced, but FIG. 3 only shows the harmonics f, $2f$ and $3f$.

Therefore, RF 40 filter should be positioned to substantially reduce the signals from tissue at the harmonics. For example, RF filter 40 might have a filtering passband between adjacent harmonics and which substantially filters out energy at the adjacent harmonics. As an addition example, RF filter 40 might have a filtering passband less than the first harmonic and which substantially filters out energy at the first harmonic.

In FIG. 3, RF filter 40 is shown as having a passband which completely filters out energy at the harmonics. It should be understood that an RF filter might pass some energy at the harmonics. However, the amount of energy at the harmonics should be substantially filtered out as compared to the center frequency of the passband. The specific amount of energy at the harmonics which should be substantially filtered out could easily be determined by a person of skill in the art, and would typically be determined in accordance with the processing power and processing complexity of the ultrasonic imaging system to distinguish signal 36 from tissue signal 38. Generally, to be practically effective in substantially filtering out energy at the harmonics, the RF filter 40 should filter out at least 50% of the energy at the harmonics. However, the present invention is not limited to this specific filtering ratio.

Therefore, regarding RF filter 40, the specific filtering passband, and the specific amount of energy around the harmonics which should be filtered out, could easily be determined by a person of skill in the art, and would typically depend on the sophistication of the ultrasonic processing performed on the received ultrasonic response.

In accordance with the above, in operation 34 of FIG. 2, ultrasonic imaging can be performed by emitting ultrasonic energy at a fundamental frequency in the myocardium, receiving a response in the myocardium generated in response to the emitted ultrasonic energy, and filtering the received response with a filter having a passband between harmonics of the fundamental frequency, or less then the first harmonic, to thereby receive a signal from microbubbles refilled in the arterioles. This technique takes advantage of the fact that when microbubbles are destroyed they emit a broadband signal, whereas tissue only generates signals around the harmonics.

Generally, with embodiments as in FIGS. 2 and 3, an arteriole signal is received between harmonics, or less then the first harmonic, where a signal from microbubbles is much greater than a tissue signal. Therefore, the signal from the microbubbles can be received without being significantly masked by the tissue signal.

The technique described in FIGS. 2 and 3 is a "destructive" imaging technique, as it relies on, and causes, the destruction of microbubbles to filter out the capillaries. More specifically, destructive ultrasonic frames at relatively high power are emitted in operation 30, to destroy microbubbles.

As an example, in operation 34 of FIG. 2, ultrasonic imaging can be performed with a power Doppler mode where wall filters effectively remove tissue flash while allowing sufficient microbubble signal. In this case, it may be necessary to trigger the imaging frame(s) during a stationary portion of the cardiac cycle due to the increased effect of motion with a multi-pulse technique. It would also be advantageous to use an adaptive wall filter which "locks on to" the tissue motion because it is the largest signal, enhancing only signals which are moving relative to the tissue. For example, a time varying wall filter determines the largest signal and removes its velocity on a point by point basis. This type of filter removes signals moving at the velocity of the tissue, including signals from the capillaries that move with the same velocity as the tissue. The use of Power Doppler mode, wall filters, and adaptive wall filters is well-known in the art of ultrasonic imaging systems.

Figure 4:
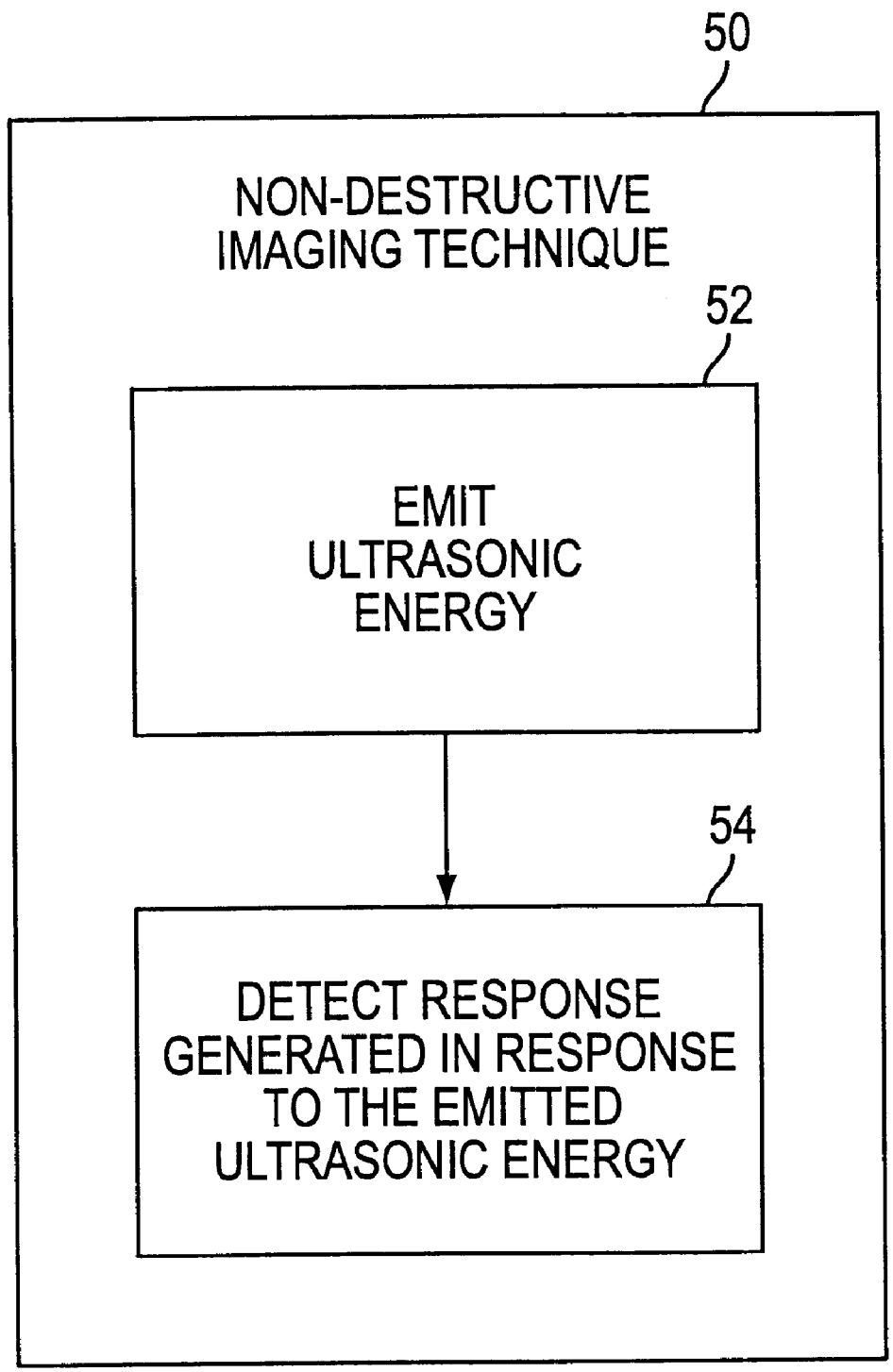
FIG. 4 is a diagram illustrating a non-destructive imaging technique, according to an additional embodiment of the present invention.

FIG. 4 is a diagram illustrating a non-destructive imaging technique 50, according to an additional embodiment of the present invention. Referring now to FIG. 4, in operation 52, ultrasonic energy is emitted into a myocardium at a relatively low power. In operation 54, a response generated in response to the emitted ultrasonic energy is received. The response includes a signal from contrast agent microbubbles and a substantially linear tissue signal. The substantially linear tissue signal is removed from the ultrasonic response, to thereby receive the signal from the microbubbles.

The non-destructive imaging techniques can be, for example, Power Modulation or Pulse Inversion. These non-destructive imaging techniques work at very low acoustic power levels such that insufficient microbubble destruction occurs and tissue signals remain substantially "linear" and can be subtracted out. Pulse Inversion and Power Modulation are multiple-pulse techniques. In many ways they are similar to color flow imaging.

In operation 54, for example, a wall filter is used to filter out unwanted tissue motion ("linear motion") while passing non-linear microbubble signals. In order for such a technique to image the arterioles, slow moving microbubbles should be removed. The wall filters can be modified such that slow moving non-linear signals are removed and faster moving non-linear signals are not removed. In operation 54, it may also be beneficial to use an adaptive wall filter technique to "lock on" to the tissue motion. With an adaptive wall filter, arterioles will not appear to be moving at the same velocity as the tissue, which is much closer to that of the capillaries.

Figure 5:
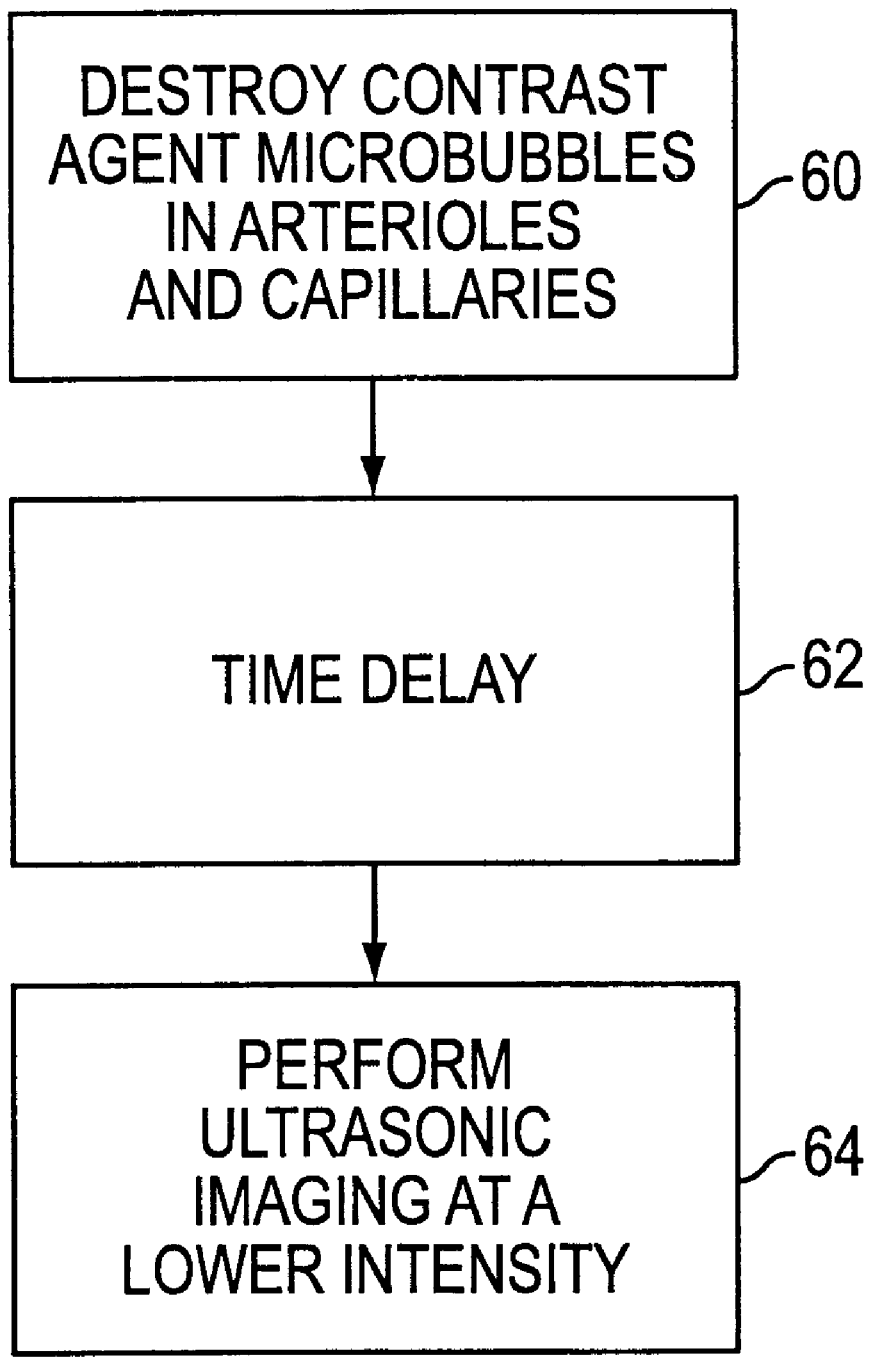
FIG. 5 is an ultrasonic imaging process using both destructive and non-destructive techniques, according to an embodiment of the present invention.

FIG. 5 is an ultrasonic imaging process using both destructive and non-destructive techniques, according to an embodiment of the present invention. Referring now to FIG. 5, in operation 60, contrast agent microbubbles in arterioles and capillaries of a myocardium are destroyed. Such destruction of microbubbles might be, for example, the same as that described in operation 30 of FIG. 2. For example, ultrasonic energy is emitted into the myocardium at an intensity sufficient to cause the microbubbles to be destroyed.

From operation 60, the process moves to operation 62, where a time delay passes from the destruction of the microbubbles. Such time delay is, for example, the same as that described in operation 32 of FIG. 2. For example, the time delay is sufficiently long to cause the arterioles to refill with microbubbles and sufficiently short so that the capillaries do not completely refill with microbubbles. As previously indicated, to achieve the required effect, the time delay might be, for example, greater than 20 ms but less than 4 s. However, the present invention is not limited to the time delay being in this specific range.

From operation 62, the process moves to operation 64, where ultrasonic imaging is performed at an intensity lower than that performed in operation 60. In operation 62, imaging might be performed, for example, in real-time.

As an example, in operation 60, ultrasonic energy is emitted with an MI greater than 0.6 to destroy contrast agent microbubbles. However, in operation 64, ultrasonic imaging is performed at an MI of, for example, less than 0.4. For example, in operation 64, MI might equal 0.1. Of course, the present invention is not limited to these specific examples of MI.

The low intensity ultrasonic imaging in operation 64 is preferably a multiple-pulse technique to suppress tissue signal. Such a technique can include, for example, Power Modulation (i.e., varying the transmit power between transmit pulses) or Phase Modulation (i.e., varying the phase between transmit pulses). With Phase Modulation, Phase Inversion (i.e., the phase difference between pulses is 180 degrees) might also be used. Power Modulation, Phase Modulation and Phase Inversion are well-known.

Further, the low intensity ultrasonic imaging in operation 64 might include, for example, varying both phase and amplitude between transmit pulses.

Moreover, the low intensity ultrasonic imaging in operation 64 might include, for example, the removal of slow moving signals (e.g., capillary signals) with wall filtering techniques. Also, an adaptive wall filtering technique might be used to substantially suppress tissue motion and bubbles moving at the same velocity as tissue (i.e., capillaries).

In addition, as will be discussed in more detail below, in operation 60, for example, destructive frames might be fired synchronous to an ECG. Moreover, the destructive frames might, for example, be fired during an isovolumic portion of the cardiac cycle.

Therefore, in FIG. 5, a destructive technique is combined with a non-destructive technique. More specifically, contrast agent microbubbles are destroyed by a high power technique and imaged in between destructive events with a real-time low power technique. This way, reflow into arterioles can be watched in real-time. Once the capillary signal has been substantially reduced, it will then be important to quantify and display the arteriole signal in such a way that it is diagnostically relevant. This would entail measuring a feature such as the cyclical variation in the arteriole signal during the cardiac cycle. Due to the pulsitile nature of the arterioles relative to the capillaries, the variation in intensity throughout the cardiac cycle is important. Also, it may be useful to measure the blood volume of arterioles by comparing the intensity to that in one of the major blood pools in the body, such as the left ventricle. Importantly, any artifacts from wall motion or thickening need to be removed if cyclic variation in arteriolar blood volume is to be measured. Therefore, it may also be helpful to measure the intensity change between systole and diastole where the heart is stationary (i.e., no motion artifacts) and to display this difference as the portion due to arteriole cyclical variation.

As indicated above, the flow in the arterioles has a pulsitile nature. Therefore, generally, the frames can be averaged across and this average can be subtracted from each frame. This would provide an improved manner of visualizing the cyclic variation. Motion compensation could be used to remove heart motion. Such motion compensation can be done automatically or manually.

Therefore, with the process in FIG. 5, a variation between systole and diastole can be compared in a region to determine the arteriole signal. The capillary signal can then be removed by subtraction of the average intensity of the systolic frames from the diastolic frames. Further, the signal from arterioles can be displayed as a color overlay.

In addition, in the embodiment in FIG. 5, cyclical backscatter might be measured within the cardiac cycle. Tissue can also be broken into segments or regions and cyclical backscatter in a region might be color coded and displayed as an overlay on a generated ultrasonic image.

As indicated above, an ECG is derived via a patient connection and ECG monitoring device. The ECG monitoring device provides an ECG signal to the ultrasonic imaging system so that the operation of the ultrasonic imaging system can be synchronized to the patient heart cycle.

Figure 6:
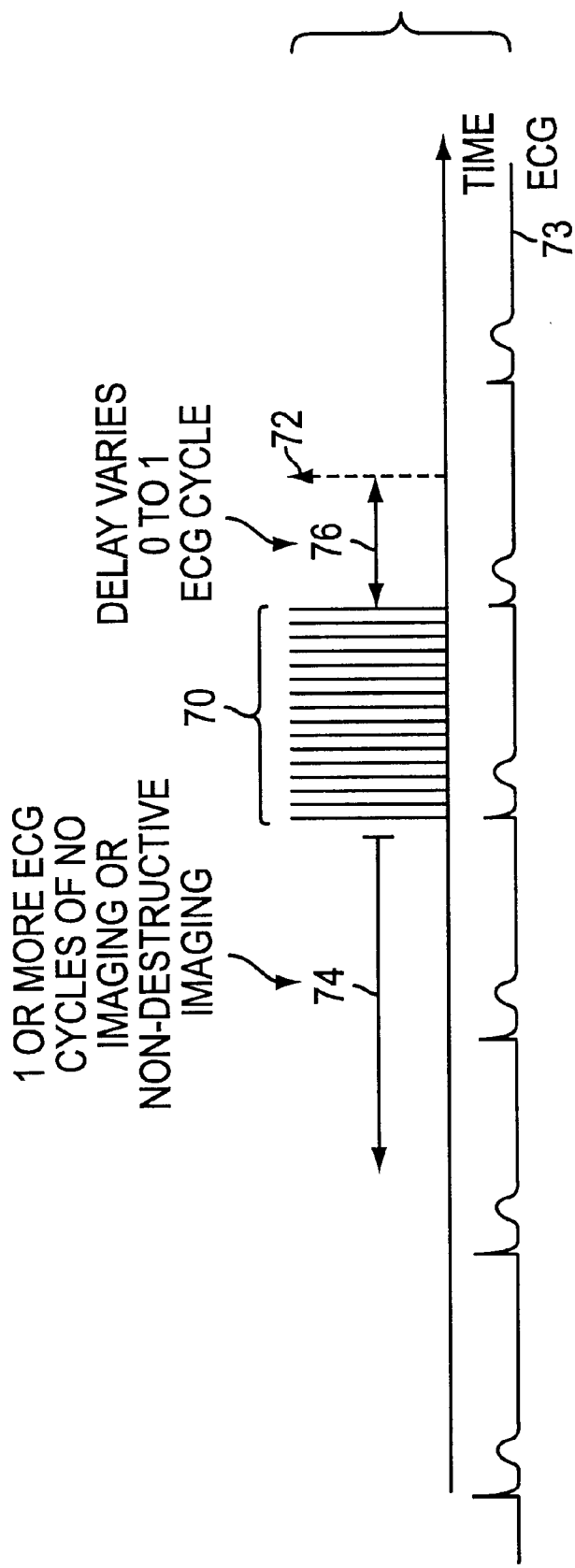
FIG. 6 is a diagram illustrating a transmission sequence of ultrasonic destructive frames and detection frames, according to an embodiment of the present invention.

FIG. 6 is a diagram illustrating a transmission sequence of ultrasonic destructive frames and detection frames, according to an embodiment of the present invention.

Referring now to FIG. 6, a series of intermittent, acoustic destructive frames 70 and then destructive or non-destructive detection frames, as indicated by a first detection frame 72, are transmitted in a sequence. Destructive frames 70 and detection frame 72 are synchronized with an ECG 73. As indicated by arrow 74, one or more ECG cycles of no imaging or non-destructive imaging may occur before transmission of destructive frames 70. The characteristics of the triggering and sequence of frames are controlled such that:

(a) Before detection imaging, a series of destructive frames 70 is fired. The amount of time (indicated by double-arrow 76) between destructive frames 70 and detection frame 72 is controlled to vary between a minimum interframe time and a time corresponding to one heart cycle. By collecting detection frames in an image memory, the detection frames may be later replayed rapidly in a manner that displays the reflow that occurs as the delay is increased from the minimum interframe time to one heart cycle.

(b) Destruction frames 70 are controlled in number or rate so as to coincide with one complete heart cycle. This ensures that all the regions of tissue that enter the imaging field of view because of heart motion will be depleted of contrast agent by destruction frames 70. This prevents heart motion from carrying contrast agent from regions out of the imaging plane into subsequent detection frames 72, thereby creating a false detection of contrast agent.

(c) Prior to the sequence of destructive frames 70, there may occur at least one (or more) heart cycles of no imaging or non-destructive imaging, as indicated by arrow 74. This ensures that the coronary blood volume contains contrast agent which has not been depleted by destructive frames 70.

(d) The sequence is repeated according to the above constraints for many heart cycles. At each occurrence of the sequence, the pre-detection interval is varied (increased) as in (a) above, such that a detection frame for each value of delay is stored for subsequent viewing.

The present invention is not limited to a trigger sequence as having destruction pulses over a complete cardiac cycle. Instead, for example, only a couple of destruction frames may be sufficient.

In the above embodiments of the present invention using both destructive frames and non-destructive frames, there are many different possible sequences in which destructive and non-destructive frames can be emitted. For example, in a simple example, one destructive frame can be emitted to destroy microbubbles, and then one non-destructive frame can be emitted to receive a response. Thus, one non-destructive frame is emitted for each destructive frame. However, various different sequences can be used. For example, in some embodiments, a plurality of destructive frames can be emitted to ensure adequate microbubble destructions, and then a plurality of non-destructive frames can be emitted to receive a response. The present invention is not limited to any specific correspondence in the number of destructive frames to the number of non-destructive frames.

Figure 7:
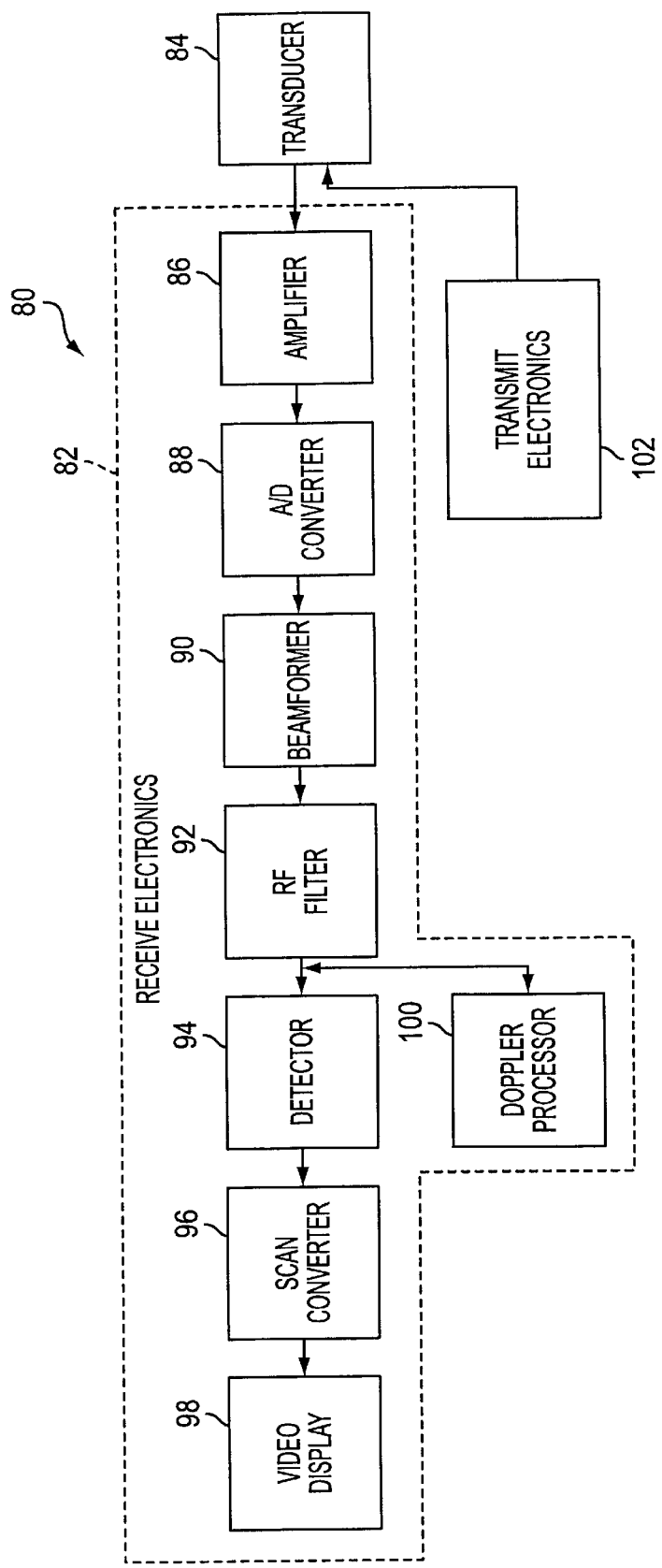
FIG. 7 is a diagram illustrating an ultrasonic imaging system, according to an embodiment of the present invention.

FIG. 7 is a diagram illustrating an ultrasonic imaging system 80, according to an embodiment of the present invention. Referring now to FIG. 7, ultrasonic imaging system 80 includes receive electronics 82 connected to a transducer 84. Receive electronics 82 includes an amplifier 86, an analog-to-digital (A/D) converter 88, a beamformer 90, an RF filter 92, a detector 94, a scan converter 96 and a video display 98. Moreover, in some embodiments, receive electronics 82 might include a Doppler processor 100 for performing required processing.

RF filter 92 would be used, for example, in embodiments described above, such as those in FIGS. 2 and 3, which use an RF filter. Doppler processor 100 would be used in embodiments described above which require Doppler processing.

Transducers, amplifiers, A/D converters, beamformers, RF filters, detectors, scan converters, video displays and Doppler processors are well-known components in the art of ultrasonic imaging systems, and the use of such components in an ultrasonic imaging system to transmit ultrasonic energy into tissue and receive a generated signal is well-known. Therefore, a detailed discussion of these components will not be presented here. Moreover, the specific arrangement of these components in FIG. 7 is only intended as an example. There are many known configurations for ultrasonic imaging systems, and the present invention is not limited to the specific configuration in FIG. 7.

FIG. 7 also illustrates transmit electronic 102 connected to transducer 84, for transmitting ultrasonic energy. Transmitting electronics 102 would be used to transmit ultrasonic energy as in various of the above-embodiments of the present invention. Transmit electronics 102 are very well-known in the art, and will not be described in detail herein. Generally, transmit electronics 102 would include a beamformer and associated electronics for transmitting appropriate ultrasonic frames.

The present invention is described above as relating to ultrasonic imaging. However, the present invention can be applied to other well-known imaging modalities, such as magnetic resonance imaging (MRI) and computed tomography (CT).

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A method comprising:
   destroying contrast agent microbubbles in arterioles and capillaries of a myocardium; and
   at a time delay from the destruction of the microbubbles which is sufficiently long to cause the arterioles to refill with microbubbles and sufficiently short so that the capillaries do not completely refill with microbubbles, performing ultrasonic imaging to receive a signal between adjacent harmonics of an ultrasonic fundamental frequency, or less than a first harmonic, from microbubbles refilled in the arterioles.

2. A method comprising:
   destroying contrast agent microbubbles in arterioles and capillaries of a myocardium;
   at a time delay from the destruction of the microbubbles which is sufficiently long to cause the arterioles to refill with microbubbles and sufficiently short so that the capillaries do not completely refill with microbubbles, performing ultrasonic imaging by
   emitting ultrasonic energy at a fundamental frequency in the myocardium,
   receiving a response in the myocardium generated in response to the emitted ultrasonic energy, and
   filtering the received response with a filter having a passband between adjacent harmonics of the fundamental frequency and which substantially filters out energy at the adjacent fundamentals, or less than a first harmonic and which substantially filters out energy at the first harmonic, to thereby receive a signal from microbubbles refilled in the arterioles.

3. A method as in claim 2, wherein said destroying comprises:
   emitting ultrasonic energy into the myocardium at an intensity causing the microbubbles to be destroyed.

4. A method as in claim 2, wherein
   said destroying comprises transmitting ultrasonic energy in destructive frames which are controlled in at least one of the group consisting of number or rate to coincide with one complete heart cycle.

5. A method as in claim 2, wherein
   said destroying comprises transmitting ultrasonic energy in destructive frames which are controlled to coincide with one complete heart cycle,
   said emitting ultrasonic energy emits ultrasonic energy in frames, and
   said time delay is from transmission of a last destructive frame in a sequence of destructive frames to emission of a first frame by said emitting, said time delay being greater than or equal to a minimum interframe time and less than or equal to a time corresponding to one heart cycle.

6. A method comprising:
   destroying contrast agent microbubbles in arterioles and capillaries of a myocardium; and
   at a time delay from the destruction of the microbubbles which is sufficiently long to cause the arterioles to refill with microbubbles and sufficiently short so that the capillaries do not completely refill with microbubbles, performing ultrasonic imaging using a power Doppler mode to receive a signal from microbubbles refilled in the arterioles.

7. A method as in claim 6, wherein said performing ultrasonic imaging receives an ultrasonic response including the signal from the microbubbles refilled in the arterioles and a tissue signal, said performing ultrasonic imaging comprising:
   wall filtering the received ultrasonic response to remove the tissue signal.

8. A method as in claim 6, wherein said performing ultrasonic imaging comprises:
   triggering ultrasonic imaging frames during a relatively stationary portion of the cardiac cycle.

9. A method as in claim 6, wherein said performing ultrasonic imaging receives an ultrasonic response including the signal from the microbubbles refilled in the arterioles and a tissue signal, said performing ultrasonic imaging further comprising:
   adaptive wall filtering the received ultrasonic response to lock onto tissue motion and thereby remove the tissue signal.

10. A method as in claim 7, wherein said performing ultrasonic imaging further comprises:
    adaptive wall filtering the received ultrasonic response to lock onto tissue motion to remove the tissue signal.

11. A method as in claim 6, wherein said destroying comprises:
    emitting ultrasonic energy into the myocardium at an intensity causing the microbubbles to be destroyed.

12. A method as in claim 6, wherein
    said destroying comprises transmitting ultrasonic energy in destructive frames which are controlled in at least one of the group consisting of number or rate to coincide with one complete heart cycle.

13. A method as in claim 6, wherein
    said destroying comprises transmitting ultrasonic energy in destructive frames which are controlled to coincide with one complete heart cycle,
    said performing ultrasonic imaging emits ultrasonic energy in frames, and
    said time delay is from transmission of a last destructive frame in a sequence of destructive frames to emission of a first frame by said performing ultrasonic imaging, said time delay being greater than or equal to a minimum interframe time and less than or equal to a time corresponding to one heart cycle.

14. A method comprising:
    transmitting ultrasonic energy into a myocardium at an intensity causing contrast agent microbubbles in arterioles and capillaries of the myocardium to be destroyed; and
    at a time delay from the destruction of the microbubbles which is sufficiently long to cause the arterioles to refill with microbubbles and sufficiently short so that the capillaries do not completely refill with microbubbles, performing ultrasonic imaging at an intensity lower than said intensity of said transmitted ultrasonic energy.

15. A method as in claim 14, wherein the ultrasonic imaging is performed to detect refilling of microbubbles in arterioles in real-time.

16. A method as in claim 14, wherein said performing ultrasonic imaging comprises:

detecting refilling of microbubbles in the arterioles in real-time, and quantifying and displaying a signal from the detected refilling.

17. A method as in claim 14, wherein said transmitting ultrasonic energy comprises transmitting ultrasonic energy in frames which are controlled in at least one of the group consisting of number or rate to coincide with one complete heart cycle.

18. A method as in claim 14, wherein said performing ultrasonic imaging comprises:

performing ultrasonic imaging using a non-destructive imaging mode to receive an ultrasonic response which includes a signal from the microbubbles and a substantially linear tissue signal, the non-destructive imaging mode removing the substantially linear tissue signal from the ultrasonic response, to thereby receive the signal from the microbubbles.

19. A method as in claim 18, wherein said performing ultrasonic imaging comprises:

wall filtering the received ultrasonic response to remove the substantially linear tissue signal.

20. A method as in claim 18, wherein said performing ultrasonic imaging comprises:

adaptive wall filtering the received ultrasonic response to remove the substantially linear tissue signal.

21. A method as in claim 18, wherein the non-destructive imaging mode is one of the group consisting of Power Modulation and Phase Modulation.

22. A method as in claim 19, wherein the non-destructive imaging mode is one of the group consisting of Power Modulation and Phase Modulation.

23. A method as in claim 20, wherein the non-destructive imaging mode is one of the group consisting of Power Modulation and Phase Modulation.

24. A method as in claim 18, wherein the non-destructive imaging mode includes a combination of Power Modulation and Phase Modulation.

25. An apparatus comprising:

means for destroying contrast agent microbubbles in arterioles and capillaries of a myocardium; and means for, at a time delay from the destruction of the microbubbles which is sufficiently long to cause the arterioles to refill with microbubbles and sufficiently short so that the capillaries do not completely refill with microbubbles, performing ultrasonic imaging to receive an ultrasonic response between harmonics of an ultrasonic fundamental frequency, or less than a first harmonic, from microbubbles refilled in the arterioles.

26. An apparatus comprising:

means for destroying contrast agent microbubbles in arterioles and capillaries of a myocardium; and means for, at a time delay from the destruction of the microbubbles which is sufficiently long to cause the arterioles to refill with microbubbles and sufficiently short so that the capillaries do not completely refill with microbubbles, performing ultrasonic imaging using a power Doppler mode to receive an ultrasonic signal from microbubbles refilled in the arterioles.

27. An apparatus comprising:

means for transmitting ultrasonic energy into a myocardium at an intensity causing contrast agent microbubbles in arterioles and capillaries of the myocardium to be destroyed; and means for, after a time delay from the destruction of the microbubbles which is sufficiently long to cause the arterioles to refill with microbubbles and sufficiently short so that the capillaries do not completely refill with microbubbles, performing ultrasonic imaging at an intensity lower than said intensity of said transmitted ultrasonic energy.

28. A method comprising:

destroying contrast agent microbubbles in arterioles and capillaries of a myocardium; and at a time delay from the destruction of the microbubbles which is sufficiently long to cause the arterioles to refill with microbubbles and sufficiently short so that the capillaries do not completely refill with microbubbles, performing an imaging modality to receive a signal between adjacent harmonics of an ultrasonic fundamental frequency, or less then a first harmonic, from microbubbles refilled in the arterioles.

29. A method as in claim 28, further comprising:

displaying an image in accordance with the received signal; and displaying cyclical backscatter via a color coded overlay on the displayed image.

30. An apparatus comprising:

an imaging device in which contrast agent is introduced in the myocardium and, in accordance with the introduced contrast agent, the imaging device including means for destroying an imageable manifestation of the contrast agent and means for, at a time delay from the destruction of the contrast agent which is sufficiently long to cause the arterioles to refill with imageable manifestation of the contrast agent and sufficiently short so that the capillaries do not completely refill with the imageable manifestation of the contrast agent, measuring a variation in the myocardium over a cardiac cycle.

31. An apparatus as in claim 30, wherein the imaging device is a magnetic resonance imaging (MRI) imaging device.

32. An apparatus as in claim 30, wherein the imaging device is a computed tomography (CT) imaging device.

* * * * *